United States Patent
Karydas

Patent Number: 5,547,594
Date of Patent: Aug. 20, 1996

[54] FLUORINATED DISULFIDE LUBRICANTS FOR POLYETHYLENE SNOW SLIDERS

[76] Inventor: Athanasios Karydas, 1365 York Ave., New York, N.Y. 10021

[21] Appl. No.: 383,355

[22] Filed: Feb. 3, 1995

[51] Int. Cl.$^6$ .................... C10M 105/50; C10M 105/72
[52] U.S. Cl. .................... 508/112; 508/128; 508/151; 508/168; 508/215; 508/570
[58] Field of Search .................... 252/48.8, 58; 568/24; C10M 105/50, 105/72, 131/00, 135/20, 135/22

[56] References Cited

U.S. PATENT DOCUMENTS

| | | | |
|---|---|---|---|
| 2,560,421 | 7/1951 | Eby | 252/48.8 |
| 2,894,991 | 7/1959 | Barr et al. | 568/24 |
| 3,006,964 | 10/1961 | Oesterling | 568/24 |
| 4,724,093 | 2/1988 | Gambaretto | 252/58 |

*Primary Examiner*—Prince Willis, Jr.
*Assistant Examiner*—Cephia D. Toomer

[57] ABSTRACT

This invention relates to lubricants for polyethylene snow sliders which comprise fluorinated disulfides of the formula $$[R_f(CH_2)_m S]_2$$

having a melting point of at least 25° C. at most 60° C., a fluorine content of at least 61% and at most 68% and wherein $R_f$ is independently a straight or branched perfluoroalkyl group.

10 Claims, No Drawings

FLUORINATED DISULFIDE LUBRICANTS FOR POLYETHYLENE SNOW SLIDERS

BACKGROUND OF THE INVENTION

This invention relates to compounds useful as lubricants for polyethylene snow sliders, such as skis, snowboards and sleds. Lubricants of this type are of particular interest as ski waxes since they reduce friction between the polyethylene running surface of the ski and the snow, which results in higher skiing speeds.

A ski in motion possesses kinetic energy and the more of this energy it maintains, the faster it will move. Some of this energy is lost through friction and is converted to heat or is lost due to the vibration of the ski. Energy is also expended for plowing and compaction which occur when the snow is compressed or pushed aside as the ski is moving. The less energy a moving ski consumes through plowing and compaction, vibration and friction, the more kinetic energy—and consequently, speed—it retains.

There are several methods of minimizing kinetic energy loss. For example, to minimize kinetic energy loss due to plowing and compaction a race course is compacted mechanically prior to the race. Vibration, which is characteristic of the ski, is reduced by the proper utilization of ski construction materials.

Kinetic energy loss due to friction can also be minimized. The following friction components may be present in a glide situation:

1. Dry friction, which occurs in areas where dry snow particles touch the ski base;

2. Capillary suction, which occurs when free water is present and adheres to the base, producing a suction effect;

3. Friction due to the presence of dirt (i.e., diesel oil, pollen, rock-dust), which occurs when atmospheric contaminants adhere to the base and the snow at the same time, connecting them and reducing speed.

Two main methods have been used to reduce kinetic energy loss due to friction:

1. Base structuring: Various textures are imprinted on the ski bases by the manufacturers and they have a dual function:

They reduce capillary suction by preventing the formation of continuous water films.

They reduce the contact area between the base and the snow.

Ski bases are made from polyethylene, a polymer ideally suited for this use due to its following properties: Excellent elasticity over the required temperature range, low cost, availability in a variety of hardness grades, ease of repair, low water absorption, and good adhesion to hydrocarbon waxes. The major disadvantage of polyethylene is that it can be damaged if heated at temperatures approaching 120° C.

2. Waxing: Ski waxes are solid lubricants that reduce friction between the ski and the snow. When selecting a wax, one optimizes the following four properties:

Hardness—The wax must always be harder than the snow so the snow does not penetrate it.

Friction coefficient—The friction coefficient must be as low as possible.

Water repellency (hydrophobicity)—Water repellency must be as high as possible.

Dirt absorption—The wax must not absorb dirt, pollen or oily atmospheric contaminants.

Until the mid-1980s, most ski waxes were hydrocarbons. Three types of hydrocarbons are typically used for ski wax production:

Paraffins (linear), which provide low friction coefficient.

Microcrystalline waxes (branched), which provide elasticity.

Synthetic (polyethylene or Fischer-Tropsch) waxes, which provide resistance to penetration by hard snow crystals.

Almost all ski waxes formulated for warm snow conditions are blends of soft paraffins and soft microcrystalline waxes. Blends of harder paraffins and microcrystalline waxes are used for more aggressive snow. Synthetic waxes are very effective wax blend hardeners so they are frequently added to wax formulations intended for use on very cold snow. Hydrocarbon ski waxes typically melt at 55° C. to 95° C. and are applied on the ski base as follows: A bar of wax is placed on a waxing iron which is heated to no more than 100° C. and wax is dripped on the ski base. The iron is then used to distribute the wax uniformly on the ski base.

In the mid-1980s, perfluorocarbon ski waxes were developed. U.S. Pat. No. 4,724,093 describes perfluorocarbon lubricants containing from 10 to 20 carbon atoms and with melting points ranging from 36° C. for $C_{10}F_{22}$ to 110° C. for $C_{16}F_{34}$. Commercially available perfluorocarbon waxes are blends with average carbon lengths of 14 to 16 and have melting points of 95° C. to 100° C. It is well known in the ski wax industry that perfluorocarbon waxes with melting points lower than 90° C. exhibit inferior performance. Perfluorocarbon waxes are applied over hydrocarbon base waxes and offer outstanding performance on wet and relatively new snows. Their good performance is attributed to their high degree of water repellency, which reduces capillary suction. Perfluorocarbon waxes also resist oil and dirt, which is attributed to their very low surface energy. This results in reduced friction on dirty snow.

Although perfluorocarbon waxes exhibit outstanding performance on wet and nonaggressive snows, they lack mechanical strength and are easily penetrated by aggressive snow crystals. As a result, skis prepared using perfluorocarbon waxes may demonstrate reduced skiing speed at snow temperatures below −8° C. Furthermore, perfluorocarbon waxes perform poorly under low humidity conditions where the water content of the snow is very low.

The application of commercial perfluorocarbon waxes also presents a problem. Their high melting points necessitate a recommended ironing temperature of 150° C. This may damage the base structure and increase friction. Furthermore, perfluorocarbons tend to sublime under these ironing conditions and this may present a significant pulmonary risk to the ski technician. Many technicians have therefore resorted to applying perfluorocarbon waxes by rubbing them on the ski base. This significantly limits durability and it is not uncommon for perfluorocarbon waxes applied by rubbing to stay on the ski base for less than several hundred meters. This can be particularly problematic during long distance cross country racing where races can be more than 20 kilometers long.

European Patent Application 0 421 303 A2 describes fluoroalcohols, fluoroesters and polyfluoroalkyl ester copolymers for use as lubricants for skis. The lubricants for skis described in the European Patent Application are not suitable for snow temperatures below −10° C.

International Application WO 94/11468 describes perfluoroalkyl terminated urethane lubricants. The compounds claimed in International Patent WO 94/11468 exhibit poor performance compared to commercial perfluorocarbon lubricants, as measured by skiing speed.

OBJECTS OF THE INVENTION

The present invention has been made in view of such drawbacks of the conventional perfluorocarbon lubricants and of the fluorinated lubricants of the prior art.

An object of this invention is to provide a lubricant for substantially reducing the friction between a polyethylene snow slider and snow over a temperature range of at least 25° C.

A further object of this invention is to provide a lubricant for reducing the friction between polyethylene snow sliders and snow without the use of waxing irons.

A third object of this invention is to provide a lubricant to reduce the friction between a polyethylene slider and snow and for the friction reduction to be effective for the duration of the sliding process.

SUMMARY OF THE INVENTION

It has now been discovered that fluorinated disulfides of the formula $$[R_f(CH_2)_mS]_2$$

wherein $R_f$ is independently a straight or branched perfluoroalkyl group, having melting points of at least 25° C. and at most 60° C. and fluorine contents of at least 61% and at most 68%, unexpectedly provide drastic reductions in friction between polyethylene sliding surfaces and snow. These friction reductions can be accomplished by applying the compounds of this invention on the sliding surface without requiring heat to achieve durability. Furthermore, the compounds of this invention are effective at snow temperatures as low as −25° C. No fluorochemical lubricants effective at such low snow temperatures are described in the literature.

The lubricants of the invention can be produced in powder or block form and can be applied on the polyethylene surface by rubbing. Alternatively, they can be dissolved in a suitable organic solvent and applied by brushing or spraying. The preferred solvents are petroleum distillates or hydrocarbon waxes dissolved in petroleum distillates and are generally employed in an amount from about 80% to about 99.5% preferably from about 97% to about 99% based on the weight of the entire formulation. The lubricants of the invention are employed at a concentration from about 0.5% to about 20% and preferably from about 1% to about 3%.

Application of the lubricants of the invention on polyethylene surface can also be accomplished by impregnating paper, nonwovens and other substrates with the lubricant and transferring the lubricant to the polyethylene surface with an iron heated to 65° C.

The lubricants of the invention can be blended with perfluorocarbon waxes and it is understood that additives that improve antistatic properties, durability, water repellency and anti-friction properties can also be used. Such additives include graphite, fluorinated graphite, molybdenum disulfide, polysiloxanes, metal alloys, and other organic or inorganic additives.

DETAILED DESCRIPTION OF THE INVENTION

Generally, suitable lubricants for polyethylene snow sliders have melting points of at least 25° C. and at most 60° C., fluorine contents of at least 61% and at most 68%, and can be represented by the formula $$[R_f(CH_2)_mS]_2$$

wherein:
$R_f$ is independently a straight or branched perfluoroalkyl group having 4 to 14 carbon atoms. If desired, the $R_f$ group can be a mixture of such moieties;
m is an integer from 2 to 4.

Preferred compounds are those with melting points of at least 30° C. and at most 55° C., fluorine contents of at least 63% and at most 68% and wherein $R_f$ is a straight or branched perfluoroalkyl group of 4 to 12 carbon atoms and m is 2.

More preferred compounds are those with melting points of at least 30° C. and at most 53° C., fluorine contents of at least 64% and at most 67% and wherein $R_f$ is a straight or branched perfluoroalkyl group of 4 to 10 carbon atoms and m is 2.

Most preferred compounds are those with melting points of at least 30° C. and at most 48° C., fluorine contents of at least 65% and at most 67% and wherein $R_f$ is a straight or branched perfluoroalkyl of 4 to 8 carbon atoms and m is 2.

The disulfide lubricants of the invention can be prepared by oxidation of fluorinated mercaptans of the formula $$R_f(CH_2)_mSH$$

with iodine in the presence of an acid catalyst or with hydrogen peroxide. Typically, the reaction is carried out in ethanol or isopropanol. The synthesis of useful mercaptans of formula $R_f(CH_2)_mSH$ is described in U.S. Pat. No. 3,655,732 and U.S. Pat. No. 3,544,633.

The disulfide lubricants of the instant invention can also be prepared by refluxing compounds of the formula $R_fCH_2CH_2SCN$ in ethanol in the presence of KOH.

In the following application descriptions, test descriptions and examples, all temperatures are given in degrees Centigrade, and all speeds are given in kilometers per hour. The examples are for illustrative purposes only.

DESCRIPTION OF LUBRICANT APPLICATION METHODS

A two-step application method was used: A "base wax" was applied as a first layer and a fluorinated "overlay" was applied as a second layer.

Commercial hydrocarbon ski waxes or commercial blends of hydrocarbon waxes with fluorinated paraffins suitable for the snow conditions were applied to the polyethylene ski bases using a waxing iron. The temperature of the iron was sufficiently high to melt the wax. The wax was uniformly distributed on the ski base by ironing. The skis were allowed to cool for at least 20 minutes and preferably eight hours and the ski bases were scraped with a plastic scraper to remove excess wax. Further smoothing was achieved by brushing with a nylon brush. Waxes constituting this first layer will be referred to in the examples as "base waxes."

The fluorinated disulfides of this invention, fluorinated lubricants of the prior art, and commercial perfluorocarbon waxes in bar form were applied by rubbing onto the base followed by polishing with a cork and brushing with a horsehair brush. Lubricants of the invention, fluorinated lubricants of the prior art, and commercial perfluorocarbon waxes available in powder form were sprinkled onto the base, rubbed using a cork until sufficiently bonded with the base wax, and the bases were brushed using a horsehair brush. The above mentioned perfluorocarbons, fluorinated lubricants of the prior art, and fluorinated disulfides will be referred to in the examples as "overlays."

DESCRIPTION OF TEST METHODS

Skiing speed evaluations were conducted on test courses, also referred to as glide tracks. Test speeds approximated those of actual competition and the length of the course was such that it could be covered in approximately 15 to 35 seconds. Multiple runs were conducted and the total time for the runs was recorded.

EXAMPLE 1

This example is comparative and illustrates the superiority of the lubricants of the invention over commercial perfluorocarbon lubricants. The test conditions were as follows:

Snow temperature: −17° C.

Air temperature: −14° C.

Relative humidity: 78%

Typical skiing speed: 100 km/h

Base wax: Red Dibloc (Toko AG, Altstatten, Switzerland)

| Ski number | Overlay | Melting point of overlay (°C.) | Total time for eight runs (sec) | Rank |
|---|---|---|---|---|
| SAL 1 | $C_yF_{2y+2}$ (commercial product with average y value of approximately 15) | 108–110 | 158.33 | 2 |
| SAL 2 | None | — | 158.59 | 3 |
| SAL 3 | $(C_6F_{13}CH_2CH_2S)_2$ | 35–37 | 157.58 | 1 |
| SAL 4 | $C_zF_{2z+2}$ (commercial product with average z value of approximately 14) | 95–100 | 158.74 | 4 |

EXAMPLE 2

This example is comparative and illustrates the superiority of the lubricants of the invention over commercial perfluorocarbon lubricants. The test conditions were as follows:

Snow temperature: −9° C.

Air temperature: −11° C.

Relative humidity: 82%

Typical skiing speed: 110 km/h

Base wax: Pilot F8 (Swix Sport, Lillehammer, Norway)

| Ski number | Overlay | Melting point of overlay (°C.) | Total time for ten runs (sec) | Rank |
|---|---|---|---|---|
| S1/S2 | $C_yF_{2y+2}$ (commercial product with average y value of approximately 15) | 108–110 | 237.12 | 2 |
| S3/S4 | $C_zF_{2z+2}$ (commercial product with average z value of approximately 14) | 95–100 | 238.06 | 3 |
| S5/S6 | $(C_6F_{13}CH_2CH_2S)_2$ | 35–37 | 236.08 | 1 |
| S7 | None | — | 239.40 | 4 |

EXAMPLE 3

This example is comparative and illustrates the superiority of the lubricants of the invention over commercial perfluorocarbon lubricants. The test conditions were as follows:

Snow temperature: −1° C.

Air temperature: 3° C.

Typical skiing speed: 100 km/h

Base wax: Yellow Dibloc (Toko AG, Altstatten, Switzerland)

| Ski number | Overlay | Melting point of overlay (°C.) | Total time for six runs (sec) | Rank |
|---|---|---|---|---|
| 1 | $C_yF_{2y+2}$ (commercial product with average y value of approximately 15) | 108–110 | 189.64 | 3 |
| 2 | $C_zF_{2z+2}$ (commercial product with average z value of approximately 14) | 95–100 | 188.58 | 2 |
| 3 | $(C_6F_{13}CH_2CH_2S)_2$ | 35–37 | 183.51 | 1 |
| 4 | None | — | 190.75 | 4 |

EXAMPLE 4

This example is comparative and illustrates the superiority of the lubricants of the invention over commercial perfluorocarbon lubricants. The test conditions were as follows:

Snow temperature: −18° C.

Air temperature: −11° C.

Relative humidity: below 40%

Typical skiing speed: 100 km/h

Base wax: Pilot F6 and C14 Polar Extreme blended in a 1 to 1 ratio (Swix Sport, Lillehammer, Norway)

| Ski number | Overlay | Melting point of overlay (°C.) | Total time for twelve runs (sec) | Rank |
|---|---|---|---|---|
| D4/D5 | $C_yF_{2y+2}$ (commercial product with average y value of approximately 15) | 108–110 | 341.80 | 4 |
| D2 | $C_zF_{2z+2}$ (commercial product with average z value of | 95–100 | 339.35 | 3 |

-continued

| Ski number | Overlay | Melting point of overlay (°C.) | Total time for twelve runs (sec) | Rank |
|---|---|---|---|---|
|  | approximately 14) |  |  |  |
| D1 | $(C_rF_{2r+1}CH_2CH_2S)_2$ wherein r has an average value of approximately 7 | 44–48 | 335.26 | 1 |
| D3 | None | — | 338.11 | 2 |

EXAMPLE 5

This example is comparative and illustrates the superiority of the lubricants of the invention over fluorinated disulfides having melting points higher than 60° C. and commercial perfluorocarbon lubricants. The test conditions were as follows:

Snow temperature: −4° C.

Air temperature: 8° C.

Typical skiing speed: 180 km/h

Base wax: Yellow Dibloc and Green Dibloc blended in a 3 to 1 ratio (Toko AG, Altstatten, Switzerland)

| Ski number | Overlay | Melting point of overlay (°C.) | Rank |
|---|---|---|---|
| 1 | $(C_qF_{2q+1}C_2CH_2S)_2$ wherein q has an average value of approximately 11 | 98–103 | 3 |
| 2 | $C_zF_{2z+2}$ (commercial product with average z value of approximately 14) | 95–100 | 2 |
| 3 | $(C_6F_{13}CH_2CH_2S)_2$ | 35–37 | 1 |

EXAMPLE 6

This example is comparative and illustrates the superiority of the lubricants of the invention over lubricants described in the prior art. The test conditions were as follows:

Snow temperature: −16° C.

Air temperature: −14° C.

Relative humidity: 50%

Typical skiing speed: 70 km/h

Base wax: S 22 (Swix Sport, Lillehammer, Norway)

| Ski number | Overlay | Melting point of overlay (°C.) | Total time for ten runs (sec) | Rank |
|---|---|---|---|---|
| 1 | $(C_rF_{2r+1}CH_2CH_2S)_2$ wherein r has an average value of approximately 7 | 44–48 | 221.09 | 1 |
| 2 | $(C_6F_{13}CH_2CH_2S)_2$ | 35–37 | 221.98 | 2 |
| 3 | $C_8F_{17}CH_2CH_2OH$ (described in EP 0 421 303 A2) | 46–50 | 225.11 | 4 |
| 4 | Adduct of two moles of $C_wF_{2w+1}CH_2CH_2OH$ wherein w has an average value of approximately 9 with one mole of isophorone diisocyanate | 51–56 | 230.48 | 5 |
| 5 | None (described in WO94/11468) | — | 223.55 | 3 |

EXAMPLE 7

This example illustrates that blends of the compounds of this invention with commercial perfluorocarbon lubricants have sufficiently low melting points as to allow ironing of the blends on the ski base without risking damage to the base from excessive heat.

| Overlay | Melting point of overlay (°C.) | Required iron temperature (°C.) |
|---|---|---|
| $(C_6F_{13}CH_2CH_2S)_2$ | 35–37 | none |
| $C_zF_{2z+2}$ (commercial product with average z value of approximately 14) | 95–100 | 130 |
| Equal parts blend of $(C_6F_{13}CH_2CH_2S)_2$ and $C_zF_{2z+2}$ (commercial product with average z value of approximately 14) | 55–70 | 100 |

What is claimed is:

1. A lubricant for polyethylene snow sliders which comprises a fluorinated disulfide of the formula $$[R_f(CH_2)_mS]_2$$

having a melting point of at least 25° C. and at most 60° C., a fluorine content of at least 61% and at most 68% and wherein $R_f$ is independently a straight or branched perfluoroalkyl group containing 4 to 14 carbon atoms or the $R_f$ group can be a mixture of such moieties; m is an integer from 2 to 4, and blended with one or more of the following: perfluorocarbons containing up to 20 carbon atoms, hydrocarbon waxes, graphite, fluorinated graphite, metal alloys, molybdenum disulfide, polysiloxanes.

2. A lubricant according to claim 1 wherein $R_f$ is a straight or branched perfluoroalkyl group of 4 to 12 carbon atoms and m is 2.

3. A lubricant according to claim 1 wherein $R_f$ is a straight or branched perfluoroalkyl group of 6 to 8 carbon atoms.

4. A lubricant according to claim 1 wherein $R_f$ is a straight or branched perfluoroalkyl group of 6 carbon atoms.

5. A method for lubricating a polyethylene snow slider having a base surface for facing the snow in use of said snow slider, comprising the step of:

applying a lubricant to said base surface, said lubricant comprises a fluorinated disulfide of $$[R_f(CH_2)_mS]_2$$

having a melting point of at least 25° C. and at most 60° C., a fluorine content of at least 61% and at most 68% and wherein $R_f$ is independently a straight or branched perfluoroalkyl group containing 4 to 14 carbon atoms, or the $R_f$ group can be a mixture of such moieties, m being an integer from 2 to 4.

6. A method as in claim 5, wherein said polyethylene snow slider is one of a ski, snowboard and sled.

7. A method as in claim 5, wherein $R_f$ is a straight or branched perfluoroalkyl group of 4 to 12 carbon atoms and m is 2.

8. A method as in claim 5, wherein $R_f$ is a straight or branched perfluoroalkyl group of 6 to 8 carbon atoms.

9. A method as in claim 5, wherein $R_f$ is a straight or branched perfluoroalkyl group of 6 carbon atoms.

10. A method as in claim 5, wherein said lubricant is in a blend with one or more of the following: perfluorocarbons containing up to 20 carbon atoms, hydrocarbon waxes, graphite, fluorinated graphite, metal alloys, molybdenum disulfide, polysiloxanes.

* * * * *